United States Patent [19]

Authelin et al.

[11] Patent Number: 6,022,985
[45] Date of Patent: Feb. 8, 2000

[54] PROCESS FOR THE PREPARATION OF 4-ACETOXY-2α-BENZOYLOXY-5β, 20-EPOXY-1, 7β-10β-TRIHYDROXY-9-OXO-TAX-11-EN-13α-YL(2R,3S)-3-TERT-BUTOXY-CARBONYLAMINO-2-HYDROXY-3-PHENYLPROPIONATE TRIHYDRATE

[75] Inventors: Jean-René Authelin, Saint Germain Les Arpajon; Jacques Doveze, Vauhallan; Elie Fouque, Saint Maur Des Fosses; Bernadette Mandard, Mareuil Sur Cher; Isabelle Taillepied, Maisons-Alfort, all of France

[73] Assignee: Rhone-Poulenc Rorer S.A., Antony Cedex, France

[21] Appl. No.: 08/776,333

[22] PCT Filed: Jul. 7, 1995

[86] PCT No.: PCT/FR95/00910

§ 371 Date: Apr. 25, 1997

§ 102(e) Date: Apr. 25, 1997

[87] PCT Pub. No.: WO96/01815

PCT Pub. Date: Jan. 25, 1996

[30] Foreign Application Priority Data

Jul. 8, 1994 [FR] France ................ 9408479

[51] Int. Cl.$^7$ .................................. C07D 305/00

[52] U.S. Cl. ............................. 549/510; 549/511
[58] Field of Search ................... 549/510, 511

[56] References Cited

U.S. PATENT DOCUMENTS 5,229,526 7/1993 Holton .................. 549/213

OTHER PUBLICATIONS

Wani et al, J. Am. Chem. Soc., 93(9), pp. 2325–2327, 1971.
Miller et al, J. Org. Chem., vol. 46, No. 7, pp. 1469–1474, 1981.

*Primary Examiner*—Ba K. Trinh
*Attorney, Agent, or Firm*—Finnegan, Henderson, Farabow, Garrett & Dunner, L.L.P.

[57] ABSTRACT

Process for the preparation of 4-acetoxy-2α-benzoyloxy-5β, 20-epoxy-1,7β, 10β-trihydroxy-9-oxo-tax-11-en-13α-yl (2R,3S)-3-tert-butoxycarbonylamino-2-hydroxy-3-phenylpropionate trihydrate, characterized in that the 4-acetoxy-2α-benzoyloxy-5β,20-epoxy-1,7β,10β-trihydroxy-9-oxo-tax-11-en-13α-yl (2R,3S)-3-tert-butoxycarbonylamino-2-hydroxy-3-phenylpropionate is crystallized from a mixture of water and an aliphatic alcohol containing 1 to 3 carbon atoms, and then the product obtained is dried under defined conditions of temperature, pressure and humidity.

5 Claims, No Drawings

PROCESS FOR THE PREPARATION OF 4-ACETOXY-2α-BENZOYLOXY-5β, 20-EPOXY-1, 7β-10β-TRIHYDROXY-9-OXO-TAX-11-EN-13α-YL(2R,3S)-3-TERT-BUTOXY-CARBONYLAMINO-2-HYDROXY-3-PHENYLPROPIONATE TRIHYDRATE

This application is a 371 of PCT/FR95/00910 dated Jul. 7, 1995.

The present invention relates to a process for the preparation of 4-acetoxy-2α-benzoyloxy-5β, 20-epoxy-1,7β,10β-trihydroxy-9-oxo-tax-11-en-13α-yl (2R,3S)-3-tert-butoxycarbonylamino-2-hydroxy-3-phenylpropionate trihydrate.

4-Acetoxy-2α-benzoyloxy-5β,20-epoxy-1,7β,10β-trihydroxy-9-oxo-tax-11-en-13α-yl (2R,3S)-3-tertbutoxycarbonylamino-2-hydroxy-3-phenylpropionate, which has remarkable anticancer and antileukaemic properties, and its preparation are described in European Patents EP-0,253,738 and EP-0,336,841.

It has been found that 4-acetoxy-2α-benzoyloxy-5β,20-epoxy-1,7β,10β-trihydroxy-9-oxo-tax-11-en-13α-yl (2R,3S)-3-tert-butoxycarbonylamino-2-hydroxy-3-phenylpropionate trihydrate has a substantially greater stability than that of the anhydrous product.

According to the invention, 4-acetoxy-2α-benzoyloxy-5β, 20-epoxy-1,7β,10β-trihydroxy-9-oxo-tax-11-en-13α-yl (2R,3S)-3-tert-butoxycarbonylamino-2-hydroxy-3-phenylpropionate trihydrate can be obtained by crystallization of 4-acetoxy-2α-benzoyloxy-5β, 20-epoxy-1,7β,10β-trihydroxy-9-oxo-tax-11-en-13α-yl (2R,3S)-3-tert-butoxycarbonylamino-2-hydroxy-3-phenylpropionate from a mixture of water and an aliphatic alcohol containing 1 to 3 carbon atoms, followed by drying of the product obtained under defined conditions of temperature, pressure and humidity.

For the implementation of the process according to the invention, it may be particularly advantageous to dissolve the 4-acetoxy-2α-benzoyloxy-5β, 20-epoxy-1,7β,10β-trihydroxy-9-oxo-tax-11-en-13α-yl (2R,3S)-3-tert-butoxycarbonylamino-2-hydroxy-3-phenylpropionate, firstly purified by chromatography, in an aliphatic alcohol containing 1 to 3 carbon atoms at a temperature preferably of between 40 and 60° C., to optionally remove the residual chromatography solvents by co-distillation under reduced pressure, replacing the volume of solvent distilled off with pure alcohol, to add optionally purified water at the same temperature, then, after optionally initiating the crystallization and cooling to a temperature close to 0° C., to separate the crystals obtained from 4-acetoxy-2α-benzoyloxy-5β, 20-epoxy-1,7β,10β-trihydroxy-9-oxo-tax-11-en-13α-yl (2R,3S)-3-tert-butoxycarbonylamino-2-hydroxy-3-phenylpropionate trihydrate crystals thus obtained, and then to dry them under reduced pressure in a controlled-humidity atmosphere.

Generally, the purified 4-acetoxy-2α-benzoyloxy-5β, 20-epoxy-1,7β,10β-trihydroxy-9-oxo-tax-11-en-13α-yl (2R,3S)-3-tert-butoxycarbonylamino-2-hydroxy-3-phenylpropionate is dissolved in an excess of the aliphatic alcohol. Preferably, the quantity of alcohol is between 8 and 12 parts by weight relative to the 4-acetoxy-2α-benzoyloxy-5β,20-epoxy-1,7β,10β-trihydroxy-9-oxo-tax-11-en-13α-yl (2R,3S)-3-tert-butoxycarbonylamino-2-hydroxy-3-phenylpropionate used.

Generally, the distillation of the alcohol is performed under reduced pressure at a temperature close to 40° C. until a thick syrup is obtained which is difficult to stir. It may be advantageous to repeat this operation several times which leads to the removal of the residual solvents contained in the purified product used.

After completing the removal of the residual solvents, the syrup obtained is taken up in a quantity of alcohol of between 3.5 and 6 parts by weight relative to the 4-acetoxy-2α-benzoyloxy-5β, 20-epoxy-1,7β,10β-trihydroxy-9-oxo-tax-11-en-13α-yl (2R,3S)-3-tert-butoxycarbonylamino-2-hydroxy-3-phenylpropionate.

After optionally separating insoluble impurities by filtration, water which is preferably purified is added such that the water/alcohol weight ratio is close to 2/1.

The crystallization is initiated and then the mixture is cooled slowly down to a temperature close to 0° C.

The 4-acetoxy-2α-benzoyloxy-5β,20-epoxy-1,7β,10β-trihydroxy-9-oxo-tax-11-en-13α-yl (2R,3S)-3-tert-butoxycarbonylamino-2-hydroxy-3-phenylpropionate trihydrate which crystallizes is separated, preferably by filtration or centrifugation, and then dried. The drying is performed under a reduced pressure of between 4 and 7 kPa, at a temperature close to 40° C. in a controlled humidity atmosphere, the relative humidity being close to 80%.

For the implementation of the process, it may be advantageous to perform the crystallization in the presence of ascorbic acid which is added during the dissolution of the purified 4-acetoxy-2α-benzoyloxy-5β,20-epoxy-1,7β,10β-trihydroxy-9-oxo-tax-11-en-13α-yl (2R,3S)-3-tert-butoxycarbonylamino-2-hydroxy-3-phenylpropionate in the alcohol. It is possible to use up to 1% by weight of ascorbic acid.

For the implementation of the process, it is particularly advantageous to use ethanol as alcohol.

The trihydrate structure of the 4-acetoxy-2α-benzoyloxy-5β, 20-epoxy-1,7β,10β-trihydroxy-9-oxo-tax-11-en-13α-yl (2R,3S)-3-tert-butoxycarbonylamino-2-hydroxy-3-phenylpropionate is confirmed by X-ray diffraction, by thermogravimetric analysis and by differential scanning calorimetry.

More particularly, thermogravimetric analysis shows a mass loss between 40 and 140° C. of 6.1%, which corresponds to three molecules of water per one molecule of 4-acetoxy-2α-benzoyloxy-5β,20-epoxy-1,7β,10β-trihydroxy-9-oxo-tax-11-en-13α-yl (2R,3S)-3-tert-butoxycarbonylamino-2-hydroxy-3-phenylpropionate.

The method for assaying the bulk water and the water of hydration by differential scanning calorimetry shows the absence of bulk water and an endothermic signal at 132.6° C. corresponds to the dissociation of a hydrate.

4-acetoxy-2α-benzoyloxy-5β, 20-epoxy-1,7β,10β-trihydroxy-9-oxo-tax-11-en-13α-yl (2R,3S)-3-tertbutoxycarbonylamino-2-hydroxy-3-phenylpropionate trihydrate exhibits the property of no longer having a hydroscopic character.

Stability studies show that 4-acetoxy-2α-benzoyloxy-5β, 20-epoxy-1,7β,10β-trihydroxy-9-oxo-tax-11-en-13α-yl (2R,3S)-3-tert-butoxycarbonylamino-2-hydroxy-3-phenylpropionate trihydrate is stable at 4° C., 25° C. and 35° C. in an atmosphere with 90% relative humidity up to 18 months without modification of its crystalline form.

Under the same conditions, anhydrous 4-acetoxy-2α-benzoyloxy-5β, 20-epoxy-1,7β,10β-trihydroxy-9-oxo-tax-11-en-13α-yl (2R,3S)-3-tert-butoxycarbonylamino-2-hydroxy-3-phenylpropionate, whose crystalline form is different, changes slowly to the trihydrate form.

The following examples illustrate the present invention.

EXAMPLE 1

303 g of 4-acetoxy-2α-benzoyloxy-5β,20-epoxy-1,7β, 10β-trihydroxy-9-oxo-tax-11-en-13α-yl (2R,3S)-3-tertbutoxycarbonylamino-2-hydroxy-3-phenylpropionate whose titre is 92.4% (0.314 mol) and 2.875 kg of absolute ethanol (d=0.79) are introduced into a reactor protected from light. The mixture is heated at 40° C. until there is complete dissolution of the 4-acetoxy-2α-benzoyloxy-5β,20-epoxy-1,7β,10β-trihydroxy-9-oxo-tax-11-en-13α-yl (2R,3S)-3-tert-butoxycarbonylamino-2-hydroxy-3-phenylpropionate. The ethanol is then distilled off at a pressure close to 12 kPa until a syrup at the stirring limit is obtained. 0.983 kg of ethanol is added to the syrup and the distillation is again performed under the same conditions. 1.257 kg of ethanol are added to the syrup obtained and heated at 50° C. until there is complete dissolution. The mixture is filtered hot and then 4.39 kg of purified water are added, over 1 hour, while the temperature is maintained at 50° C. After having initiated the crystallization, the mixture is cooled to 0° C. over 4 hours. The crystals are separated by filtration, washed with 0.909 kg and then 0.606 kg of an ethanol-water mixture (1–2 by weight) and then dried at 38° C. under reduced pressure (5.07 kPa) in an atmosphere at 80% relative humidity for 48 hours. 266.5 g of 4-acetoxy-2α-benzoyloxy-5β,20-epoxy-1,7β,10β-trihydroxy-9-oxo-tax-11-en-13α-yl (2R,3S)-3-tert-butoxycarbonylamino-2-hydroxy-3-phenylpropionate trihydrate are thus obtained whose analysis shows that its high-performance liquid chromatography titre is 98.7% (on a dry basis) and that the water content is 6.15%.

EXAMPLE 2

110.0 g of 4-acetoxy-2α-benzoyloxy-5β,20-epoxy-1,7β,10β-trihydroxy-9-oxo-tax-11-en-13α-yl (2R,3S)-3-tert-butoxycarbonylamino-2-hydroxy-3-phenylpropionate with a titre of 92.5% and 0.2224 g of ascorbic acid are dissolved, at a temperature close to 35° C., in 1340 cm³ of ethanol. About 70% of the ethanol introduced is distilled off under reduced pressure (8 kPa) at a temperature close to 20° C. The mixture [lacuna] heated to 50° C. and then filtered. The filter is washed with 3 times 70.5 cm³ of ethanol and then 860.5 cm³ of purified water are added over 15 minutes at 50° C. The mixture is seeded with a few crystals of 4-acetoxy-2α-benzoyloxy-5β, 20-epoxy-1,7β,10β-trihydroxy-9-oxo-tax-11-en-13α-yl (2R,3S)-3-tert-butoxycarbonylamino-2-hydroxy-3-phenylpropionate trihydrate and then stirred for 30 minutes. 860.5 cm³ of purified water are then added over 3 hours at 50° C. and then cooled over 3 hours down to a temperature close to 0° C. The slurry is then filtered. The filtration cake is washed with 330 g of a water-ethanol mixture (2–1 by weight) and then with 220 g of the same mixture and then dried under reduced pressure (5 kPa) at 38° C. under an atmosphere at 80% relative humidity. 110.2 g of 4-acetoxy-2α-benzoyloxy-5β,20-epoxy-1,7β,10β-trihydroxy-9-oxo-tax-11-en-13α-yl (2R,3S)-3-tert-butoxycarbonylamino-2-hydroxy-3-phenylpropionate trihydrate are thus obtained with a yield of 98%.

We claim:

1. A process for the preparation of 4-acetoxy-2α-benzoyloxy-5β,20-epoxy-1,7β,10β-trihydroxy-9-oxo-tax-11-en-13α-yl (2R,3S)-3-tertbutoxycarbonylamino-2-hydroxy-3-phenylpropionate trihydrate, comprising crystallizing said 4-acetoxy-2α-benzoyloxy-5β,20-epoxy-1,7β,10β-trihydroxy-9-oxo-tax-11-en-13α-yl (2R,3S)-3-tert-butoxycarbonylamino-2-hydroxy-3-phenylpropionate trihydrate from a mixture of water and an aliphatic alcohol containing 1 to 3 carbon atoms, and then drying the product obtained under defined conditions of temperature, pressure, and humidity.

2. The process according to claim 1, wherein the water/alcohol weight ratio is about 2/1.

3. The process according to claim 1, wherein said alcohol is ethanol.

4. The process according to claim 1, wherein said drying step is performed at a temperature of about 40° C., at a pressure of from about 4 to about 7 kPa and in an atmosphere whose relative humidity is about 80%.

5. The process according to claim 1, wherein said crystallizing step is performed in the presence of ascorbic acid.

* * * * *